United States Patent [19]

McLeod et al.

[11] Patent Number: 5,103,806
[45] Date of Patent: Apr. 14, 1992

[54] METHOD FOR THE PROMOTION OF GROWTH, INGROWTH AND HEALING OF BONE TISSUE AND THE PREVENTION OF OSTEOPENIA BY MECHANICAL LOADING OF THE BONE TISSUE

[75] Inventors: Kenneth J. McLeod, Setauket; Clinton T. Rubin, Port Jefferson, both of N.Y.

[73] Assignee: The Research Foundation of State University of New York, Albany, N.Y.

[21] Appl. No.: 560,186

[22] Filed: Jul. 31, 1990

[51] Int. Cl.⁵ ............................................. A61N 1/00
[52] U.S. Cl. ........................... 128/24 AA; 128/419 F
[58] Field of Search ..................... 128/419 F, 24 AA

[56] References Cited

U.S. PATENT DOCUMENTS

| | | |
|---|---|---|
| 3,890,953 | 6/1975 | Kraus . |
| 3,915,151 | 10/1975 | Kraus . |
| 4,066,065 | 1/1978 | Kraus . |
| 4,105,017 | 8/1978 | Ryaby et al. . |
| 4,266,532 | 5/1981 | Ryaby et al. . |
| 4,266,533 | 5/1981 | Ryosy et al. ................... 128/419 F |
| 4,306,564 | 12/1981 | Kraus ............................. 128/419 F |
| 4,343,303 | 8/1982 | Williams . |
| 4,530,360 | 7/1985 | Duarte . |
| 4,538,596 | 9/1985 | Colasante . |
| 4,753,225 | 6/1988 | Vögel . |

OTHER PUBLICATIONS

"Attempt to Stimulate Longitudinal Growth in the Dog by Mechanical Vibration," Elson, R.A., et al., p. 406.
"Generation of Electric Potentials by Bone in Response to Mechanical Stress," Bassett, et al., pp. 137, 1063–1064.

*Primary Examiner*—Ruth S. Smith
*Attorney, Agent, or Firm*—Hoffmann & Baron

[57] ABSTRACT

A method for preventing osteopenia, promoting bone tissue growth, ingrowth, and healing of bone tissue includes the step of applying a mechanical load to the bone tissue at a relatively low level on the order of between about 50 and about 500 microstrain, peak-to-peak, and at a relatively high frequency in the range of about 10 and about 50 hertz. Mechanical loading at such strain levels and such frequencies has been found to prevent bone loss and enhance new bone formation.

3 Claims, No Drawings

METHOD FOR THE PREPARATION OF GROWTH, INGROWTH AND HEALING OF BONE TISSUE AND THE PREVENTION OF OSTEOPENIA BY MECHANICAL LOADING OF THE BONE TISSUE

BACKGROUND OF THE INVENTION

1. Field Of The Invention

This invention generally relates to a method of inducing strain in bone tissue, and more specifically relates to a method for preventing osteopenia, and promoting growth, ingrowth and healing of bone tissue by mechanically loading the bone tissue.

2. Description Of The Prior Art

Numerous publications and patents disclose various methods of maintaining or promoting bone tissue growth. For example, Ryaby, et al. U.S. Pat. Nos. 4,105,017, 4,266,532, 4,266,533 and 4,315,503 collectively describe means and methods for inducing voltage and current signals in bone tissue for the treatment or repair of bone fractures. Kraus, et al. U.S. Pat. No. 3,890,953 discloses stimulating the healing of fractures by the application of magnetic fields, the effect of which is described as introducing mechanical stress.

U.S. Pat. No. 4,530,360 which issued to Luiz Duarte discloses a method for healing bone fractures by the application of ultrasound. Also, the piezoelectric response of mechanically stressed bone is disclosed in the article, *Generation of Electric Potentials by Bone in Response to Mechanical Stress*, published in Science Magazine 137, 1063–1064, Sept. 28, 1962.

Many conventional methods of promoting bone tissue growth and bone maintenance by the application of mechanical loads generally tend to apply relatively low frequency or low repetition rate, relatively high magnitude loading. Such loading not only may not be necessary but also may be detrimental to bone maintenance and well being.

The maintenance of bone mass is commonly believed to be regulated by the peak loads experienced by the bone. Thus, prescribed techniques for mineralization include aggressive exercise or even impact loading, for example, heel drops. For the elderly, these treatment protocols can be difficult to maintain or even dangerous. High loading activity could precipitate the fracture that the exercise was supposed to prevent.

OBJECTS AND SUMMARY OF THE INVENTION

It is an object of the present invention to provide a method for preventing osteopenia, promoting growth, ingrowth, and healing of bone tissue by a mechanical loading protocol.

It is another object of the present invention to provide a method for bone tissue growth and maintenance whereby low level strains at relatively physiologically high frequencies are introduced into bone tissue by mechanical loading techniques.

It is yet another object of the present invention to provide a method for maintaining bone mass and healing fractures which utilizes relatively low level, high repetition rate or frequency mechanical loading of the bone tissue.

It is a further object of the present invention to provide a method for maintaining bone mass, for accelerating fracture healing and promoting bone growth and ingrowth by mechanically loading the bone tissue.

In accordance with one form of the present invention, a method for preventing osteopenia, promoting growth, ingrowth, and healing of bone tissue comprises the step of applying a physiologically based relatively high frequency, relatively low level mechanical load to the bone tissue. One preferred frequency range of the mechanical load on the bone tissue is between about 10 and about 50 hertz, and the preferred peak-to-peak level of the mechanical load is on the order of between about 50 and about 500 microstrain. Mechanical loading on bone tissue at strains of this level and induced within the frequency range set forth above can prevent bone loss and enhance new bone formation. Such mechanical loading of the bone tissue may be introduced by using various apparatus, including vibrating floor plates and chairs, electrical stimulation of muscles, isometric exercises, modulated ultrasound, or transducers attached to the skin or external fixation devices to focus energy at the fracture site. These transcutaneous signals, for example passed through a bone condyle, will focus energy at the fracture site.

These and other objects, features and advantages of the present invention will be apparent from the following detailed description of illustrative embodiments thereof.

DETAILED DESCRIPTION OF THE PREFERRED EMBODIMENTS

Osteopenia, i.e., the loss of bone mass, arises to a large degree from a decrease in muscle activity, such as due to bed rest or old age. This loss can be prevented, or even reversed, if the effect of muscle activity on bone can be mimicked. The inventors have isolated and characterized a high frequency acoustic vibration arising from the impact of individual muscle cells during contraction, which create mechanical, frequency specific, low level oscillations in the subjacent bones. Using in vivo studies, the inventors have discovered that extremely low level strains induced within this physiologically based frequency range can prevent bone loss or even enhance new bone formation.

In accordance with the present invention, a method for preventing osteopenia, and promoting growth, ingrowth and healing of bone tissue comprises the step of inducing a relatively low level, physiologically based relatively high frequency strain in the bone tissue, preferably by mechanically loading the bone. Fundamental and primary harmonic frequencies induced in the bone by conventional mechanical loading techniques, such as through walking or jogging, are in the range of between 1 and 10 hertz. However, the inventors have discovered that the higher frequency by-products of such loading, such as caused by muscle contractions, in the "hyperphysiologic" frequency range of about 10 to about 100 hertz, can have beneficial effects in bone tissue, even when applied at extremely low intensities.

Accordingly, the frequency range of the mechanical strain applied to the bone is preferably between about 10 and about 100 hertz and is more preferably between about 10 and about 50 hertz. The magnitude or peak-to-peak level of the strain induced in the bone tissue is preferably between about 10 and about 1000 microstrain and is more preferably between about 50 and about 500 microstrain at the above-mentioned frequency ranges. The optimal frequency of the mechanical strain is between about 15 hertz and about 25 hertz, and the optimal peak-to-peak level of the load induced in the bone tissue is about 100 microstrain at the optimal frequency range.

The frequency ranges disclosed above are significantly higher than conventional bone treatment protocols while the strain magnitudes are much lower. For example, a program of exercise involving walking or running involves the application of mechanical loading at about 1 or 2 hertz in frequency or repetition rate. Very little energy is transmitted to the bone tissue at the higher level harmonics of this frequency, that is, within the preferred 10 to 50 hertz bandwidth, to stimulate bone tissue cell activity. As a result, such exercise programs are required to be maintained over an extended period of time. Furthermore, aggressive exercise or even impact loading used as bone tissue treatment protocols may be difficult to maintain or even dangerous, especially for the elderly. High loading activity could precipitate the fracture that the exercise was supposed to prevent.

The method of the present invention, on the other hand, with its application of lower magnitude mechanical strains at significantly higher frequencies, minimizes the possibility of fracturing or harming the bone tissue, and further minimizes the period of time over which such mechanical loading need be applied. It is believed that about 5 to about 60 minutes per day of exposure to mechanical strains between a frequency of about 10 and about 50 hertz and a load level of between about 50 and about 500 microstrain will sufficiently induce the appropriate energy into the bone tissue to stimulate the bone tissue cell activity.

The inventors conducted experiments on various animals, in vivo, in which a 500 microstrain peak-to-peak load at a 1 hertz frequency was applied to a control group, and a 500 microstrain peak-to-peak load at a frequency of 15 hertz was applied to another group of animals. The control group exhibited a bone loss of between 10% and 15%, which would correspond to a normal 10% loss in bone mass normally expected through disuse. On the other hand, the animals to which a mechanical load of 500 microstrain at a frequency of 15 hertz was applied exhibited an average increase in bone mass of 30%.

The method of the present invention overcomes the inherent disadvantages of conventional mechanical loading, bone treatment protocols. It is less dangerous and more easily applied to the patient, especially the elderly. The lower level of the mechanical strain minimizes the chance of injury to the patient and the bone tissue being treated, and the higher frequency range of the loading significantly reduces the period of time required for such mechanical exposure. Finally, it would appear that bone and connective tissue is acutely responsive to strains induced in the above-mentioned frequency ranges.

The method of the present invention is applicable not only to preventing osteopenia, but also for treatment of fractures by "dynamizing" the fracture, that is, by putting energy into the fracture which causes minute flexing of the bone rather than by keeping the bone rigid, as is the conventional method of bone healing. The invention can also be applied to promote osseointegration, whereby bone need be encouraged to grow into prosthetic implants or bone grafts.

The method of the present invention may be implemented by a number of devices and techniques, including vibrating floor plates and chairs, electrical stimulation of muscles, isometric exercises, modulated ultrasound, or transducers attached to the skin or external fixation devices to focus energy at the fracture site. These transcutaneous signals, for example passed through a bone condyle, will focus energy at the fracture site.

Although illustrative embodiments of the present invention have been described herein, it is to be understood that the invention is not limited to those precise embodiments, and that various other changes and modifications may be effected therein by one skilled in the art without departing from the scope or spirit of the invention.

What is claimed is:

1. A method for preventing osteopenia, as well as for promoting growth, ingrowth and healing of bone tissue, which comprises the step of:
    subjecting the bone tissue to a mechanical load sufficient to cause a strain in the bone tissue at a relatively low level of between about 10 and about 1000 microstrain, peak-to-peak, and at a relatively high frequency of between about 10 and about 100 hertz.

2. A method for preventing osteopenia, as well as for promoting bone tissue growth, ingrowth and healing of bone tissue, which comprises the step of:
    subjecting the bone tissue to a mechanical load sufficient to cause strain in the bone tissue at a relatively low level of between about 50 and about 500 microstrain, peak-to-peak, and at a relatively high frequency of between about 10 and about 50 hertz.

3. A method as defined by claim 2, wherein the mechanical load applied causes a strain in the bone tissue of about 100 microstrain, peak-to-peak and is at a frequency of between about 15 and about 25 hertz.

* * * * *